(12) United States Patent
Ayres (10) Patent No.: US 7,435,941 B2
(45) Date of Patent: Oct. 14, 2008

(54) METHODS FOR MEASURING OPTICAL CHARACTERISTICS BY DIFFERENTIAL DIFFRACTIVE SCANNING

(75) Inventor: Mark R. Ayres, Boulder, CO (US)

(73) Assignee: InPhase Technologies, Inc., Longmont, CO (US)

( * ) Notice: Subject to any disclaimer, the term of this patent is extended or adjusted under 35 U.S.C. 154(b) by 225 days.

(21) Appl. No.: 10/800,111

(22) Filed: Mar. 12, 2004

(65) Prior Publication Data

US 2005/0018180 A1    Jan. 27, 2005

Related U.S. Application Data

(60) Provisional application No. 60/455,325, filed on Mar. 14, 2003.

(51) Int. Cl.
*H01J 40/14* (2006.01)

(52) U.S. Cl. .................................. 250/221; 356/239.1

(58) Field of Classification Search ............. 356/239.1, 356/239.2, 239.3, 239.4, 239.5; 250/559.43, 250/559.42, 559.44, 559.29, 221
See application file for complete search history.

(56) References Cited

U.S. PATENT DOCUMENTS

| | | | |
|---|---|---|---|
| 3,688,235 A * | 8/1972 | Migeotte | 250/559.4 |
| 4,453,827 A | 6/1984 | Taboada | |
| 4,952,027 A * | 8/1990 | Saito et al. | 356/432 |
| 5,042,952 A * | 8/1991 | Opsal et al. | 356/432 |
| 5,181,080 A * | 1/1993 | Fanton et al. | 356/128 |
| 5,210,592 A * | 5/1993 | Bretschneider | 250/559.42 |
| 5,737,081 A | 4/1998 | Freischlad | |
| 6,034,766 A * | 3/2000 | Sugiura et al. | 356/239.1 |
| 6,134,011 A * | 10/2000 | Klein et al. | 250/225 |
| 2002/0031290 A1 * | 3/2002 | Tsutsumi | 385/1 |
| 2002/0048233 A1 * | 4/2002 | Ogasawara et al. | 369/44.23 |
| 2003/0147327 A1 | 8/2003 | Curtis et al. | |
| 2004/0027668 A1 | 2/2004 | Ayres et al. | |

OTHER PUBLICATIONS

Ayres, M.R. et al. (Nov. 20, 2006). "Scanning Transmission Microscopy Using A Position-Sensitive Detector," *Applied Optics* 45(33):8410-8418.

Ayres, M.R. (2007). "Signal Modulation For Holographic Memories," Doctor of Philosophy Thesis submitted to the Department of Electrical and Computer Engineering, Graduate School of the University of Colorado, 252 pages.

(Continued)

*Primary Examiner*—Georgia Y. Epps
*Assistant Examiner*—Kevin Wyatt
(74) *Attorney, Agent, or Firm*—Morrison & Foerster LLP (57) ABSTRACT

Methods and systems for measuring and/or inspecting a characteristic of an optical article are provided. In one example, a method includes illuminating an optical article with a focused beam of light, detecting the light with a sensor after interacting with the optical article, determining a deflection angle of the beam of light, and determining a characteristic of the optical article based on the deflection angle. In one example, a system includes a light source, an optical element, and a sensor. The optical element focuses light from the light source to a reference location, the sensor detects the light from the reference location and generates signals associated with the intensity and position of the light received. A processor may receive the signals from the sensor and thereby determine a deflection angle of the light from the probe path.

28 Claims, 8 Drawing Sheets

OTHER PUBLICATIONS

Frieden, B.R. (Jan. 1967). "Optical Transfer of the Three-Dimensional Object," *Journal of the Optical Society of America* 57(1):56-66.

Kawata, Y. et al. (May 10, 1996). "Differential Phase-Contrast Microscope With Split Detector for the Readout System of a Multilayered Optical Memory," *Applied Optics* 35(14):2466-2470.

Kogelnik, H. (Nov. 1969). "Coupled Wave Theory for Thick Hologram Gratings," *The Bell System Technical Journal* 48(9):2909-2947.

O'Byrne, J.W. et al. (1999). "Adaptive Optics in Confocal Microscopy," *World Scientific*, six pages.

Sheppard, C.J.R. et al. (1977). "Image Formation in the Scanning Microscopes," *Optica Acta* 24(10):1051-1073.

Sheppard, C.J.R. et al. (Sep. 1978). "Depth of Field in the Scanning Microscope," *Optics Letters* 3(3):115-117.

Sheppard, C.J.R. et al. (Sep. 1989). "Three-Dimensional Imaging in a Microscope," *J. Opt. Soc. Am. A* 6(9):1260-1269.

Sheppard, C.J.R. et al. (Feb. 1994). "Three-Dimensional Transfer Functions for High-Aperture Systems," *J. Opt. Soc. Am. A* 11(2):593-598.

Streibl, N. (Feb. 1985). "Three-Dimensional Imaging by a Microscope," *J. Opt. Soc. Am. A* 2(2):121-127.

\* cited by examiner

METHODS FOR MEASURING OPTICAL CHARACTERISTICS BY DIFFERENTIAL DIFFRACTIVE SCANNING

CROSS-REFERENCE TO RELATED APPLICATIONS

The present application claims benefit of earlier filed provisional application U.S. Ser. No. 60/455,325, entitled "METHOD FOR MEASURING OPTICAL QUALITY BY DIFFERENTIAL DIFFRACTIVE SCANNING," filed on Mar. 14, 2003, which is hereby incorporated by reference as if fully set forth herein.

BACKGROUND

1. Field of the Invention

The invention relates generally to methods and systems for optical inspection and measurement techniques, and more particularly to methods and systems for inspecting and measuring surface and/or volume characteristics of transmissive and/or reflective optical articles.

2. Description of the Related Art

Many optical devices and systems include optical articles having desired optical characteristics and tolerances relating to, e.g., surface flatness and defect characteristics such as divots or peaks on optical surfaces as well as refractive index values of transmissive articles. The performance of an optical article is typically highly dependent on the quality of the optical surfaces and index values of the article. For example, optically flat surfaces may have desired tolerances relating to the smoothness and relative size of defects on the surface, where variations from the desired tolerances degrade the article performance. Both fine scale smoothness, and coarse scale deviations from the design target are factors of the article performance. Additionally, performance of transmissive optical articles is generally dependent on index homogeneity within the article (or in the case of a gradient index, or "GRIN," element on the error between the intended index values versus the actual index values). Accordingly, it is desirable to inspect optical surface characteristics and volume characteristics of optical articles to determine if they are within desired tolerances for a particular use or application.

Optical articles may be inspected for small and large scale defects in many ways. Most commonly, an interferometer is used to test the wavefront emerging from a surface of an optical article. A variety of commercially available interferometer systems are used for this purpose. Exemplary systems commonly include Fizeau or Twyman-Green type interferometers that measure the distortion of surfaces or transmitted wavefronts as is known in the art. Such systems do not include any physical contact with the optical article that is under inspection and are particularly useful for testing or inspecting surfaces of computer disks, silicon wafers/structures, and the like.

Generally, interferometer systems include a laser that produces a coherent light beam which is expanded by the combination of a focusing lens and a collimator lens into a collimated light beam. The collimated light beam is then divided into two beams of equal intensity, e.g., by a 50% reflecting beam splitter in the path of the collimated light beam. A first beam reflects from the surface of the optical article under inspection and a second beam reflects from a reference surface. The beam transmitted through or reflected from the article is the test beam and the beam reflected from the reference surface serves as a reference beam. The test beam and the reference beam are combined and directed together toward an imaging lens and a sensor. The sensor detects the two beams and interference fringes associated with variations in the surface of the optical article under inspection relative to the reference surface. In particular, the interference patterns may be analyzed to provide information regarding the smoothness of the surface and defect features of the surface such as grooves, divots, peaks, and the like.

Interferometer systems and methods have several disadvantages for inspecting the optical quality of articles. For example, the interferometer system includes relatively expensive equipment, and generally must be dimensionally stable to less than the wavelength of the light being used in order to accurately observe the interference fringes. Additionally, interferometer methods compare the optical article under inspection to a reference object/surface such that inspection accuracy depends in large part on the reference object. The reference object is therefore generally made to high precision standards, often at substantial cost. Also, fine-pitched features (e.g., surface roughness) are generally not well resolved with interferometer methods and systems. Finally, interferometer methods generally do not allow for inspection or measurements of characteristics of the volume of the optical article, e.g., to determine index homogeneity or other characteristics at image planes within one or more layers of a transmissive and/or reflective optical article.

BRIEF SUMMARY

In one aspect of the present invention, systems for measuring and/or inspecting a characteristic of an optical article are provided. In one example of this aspect, a system includes a light source, an optical element, and a sensor. The optical element focuses light from the light source along a probe path to a reference location associated with an expected position of an optical article. The sensor detects the light from the reference location and generates signals associated with the intensity and position of the light received. A processor may receive the signals from the sensor and thereby determine a deflection angle of the light from the probe path. The reference location may be associated with an expected position of a surface or volume of an optical article.

The system may further include a stage for translating an optical article relative to the light source and the probe path in one, two, or three dimensions. The processor may determine a characteristic of the optical article based on the deflection angle of the light at multiple locations of the optical article. The characteristic may include surface flatness, a divot feature, a peak feature, an index of refraction value, or the like. In other examples, the characteristic may include stored information.

The sensor may include a segmented detector such as a quadrant photodetector or the like to determine light deviation. The sensor may also include a position sensitive diode device or other suitable detector. The system may also include a confocal imaging system, e.g., including a focusing element and pin-hole filter.

In another aspect of the present invention, methods for measuring a characteristic of an optical article are provided. In one example, a method includes illuminating an optical article with a focused beam of light along a probe path, detecting the light with a sensor after the light interacts with the optical article, determining a deflection angle of the beam of light with respect to the probe path after interacting with the optical article, and determining a characteristic of the optical article based on the deflection angle.

The method may further include translating the optical article relative to the probe path and detecting multiple deflection angles at different locations. The method may further include producing a surface relief pattern, equivalent single surface plot, or volumetric index map from the multiple deflection angles.

In another example, a method includes scanning an optical article with a focused beam of light, detecting a deflection angle of the focused beam of light from the optical article at multiple scan positions, and determining a characteristic of the optical article based on the deflection angles at the multiple scan positions.

The present invention is better understood upon consideration of the detailed description below in conjunction with the accompanying drawings and claims.

DETAILED DESCRIPTION

Methods and systems are provided for measuring optical characteristics of optical articles such as surface flatness, surface defects, volume index variations, and the like through differential diffractive measurements and scanning. The following description is presented to enable any person of ordinary skill in the art to make and use the invention. Descriptions of specific techniques and applications are provided only as examples. Various modifications to the examples described herein will be readily apparent to those of ordinary skill in the art, and the general principles defined herein may be applied to other examples and applications without departing from the spirit and scope of the invention. Thus, the present invention is not intended to be limited to the examples described and shown, but is to be accorded the widest scope consistent with the principles and features disclosed herein.

In one example of a differential diffractive scanning technique, a probe beam of electromagnetic radiation emanating from, e.g., a laser, is focused to a reference location or spot upon or within an optical article to be inspected. The local region of the article illuminated by the probe beam causes diffraction (or refraction) of the probe beam passing through or reflected from a portion of the optical article. The expanding beam emerges from the article and is received by a sensor. In this system and method, small variations in the surface angle or roughness of the article will change the angle of the beam as it interacts with the article. The sensor, e.g., a quadrant photodetector, position sensor diode, or the like, can be used to precisely measure the position of the beam incident upon the sensor, e.g., by measuring the intensity centroid of the beam or other suitable value relating to the beam position. The position of the beam incident the sensor may then be used to determine the angular deflection of the beam caused by the illuminated region of the optical article.

The optical article under test may be mechanically scanned by the exemplary system and signals from the sensor analyzed at a plurality of x, y (and in some examples z) coordinates to create images or profiles of the surface topology (or volume/index characteristics). For example, an analyzer unit including, e.g., the sensor and a processor, receives the probe beam and establishes beam deflections by the optical article for each inspection point. The processor may provide recognizable surface characteristics associated with the beam deflection information and correlate these characteristics with the plurality of scanned locations of the optical article to provide information regarding characteristics of the article such as surface flatness, defects, index variations, and the like.

The scan samples may be plotted directly (e.g., with a false color map vs. scan position or the like), or analyzed in other suitable manners to determine performance metrics associated with the optical article. In one example, the data may be used in numerical integration and combination to form an "equivalent single surface"—a calculated surface relief pattern that would give a diffraction pattern most consistent with the observed data. A fixed-thickness equivalent index profile may similarly be derived. Additionally, the sensor sum may be collected to determine the local transmissivity (or reflectivity) of the optical article.

The following description includes various aspects and examples of the present invention. As will be recognized by those of ordinary skill in the art various examples may be used alone or in combination with various other methods and systems depending, for example, on the particular application.

Figure 1:
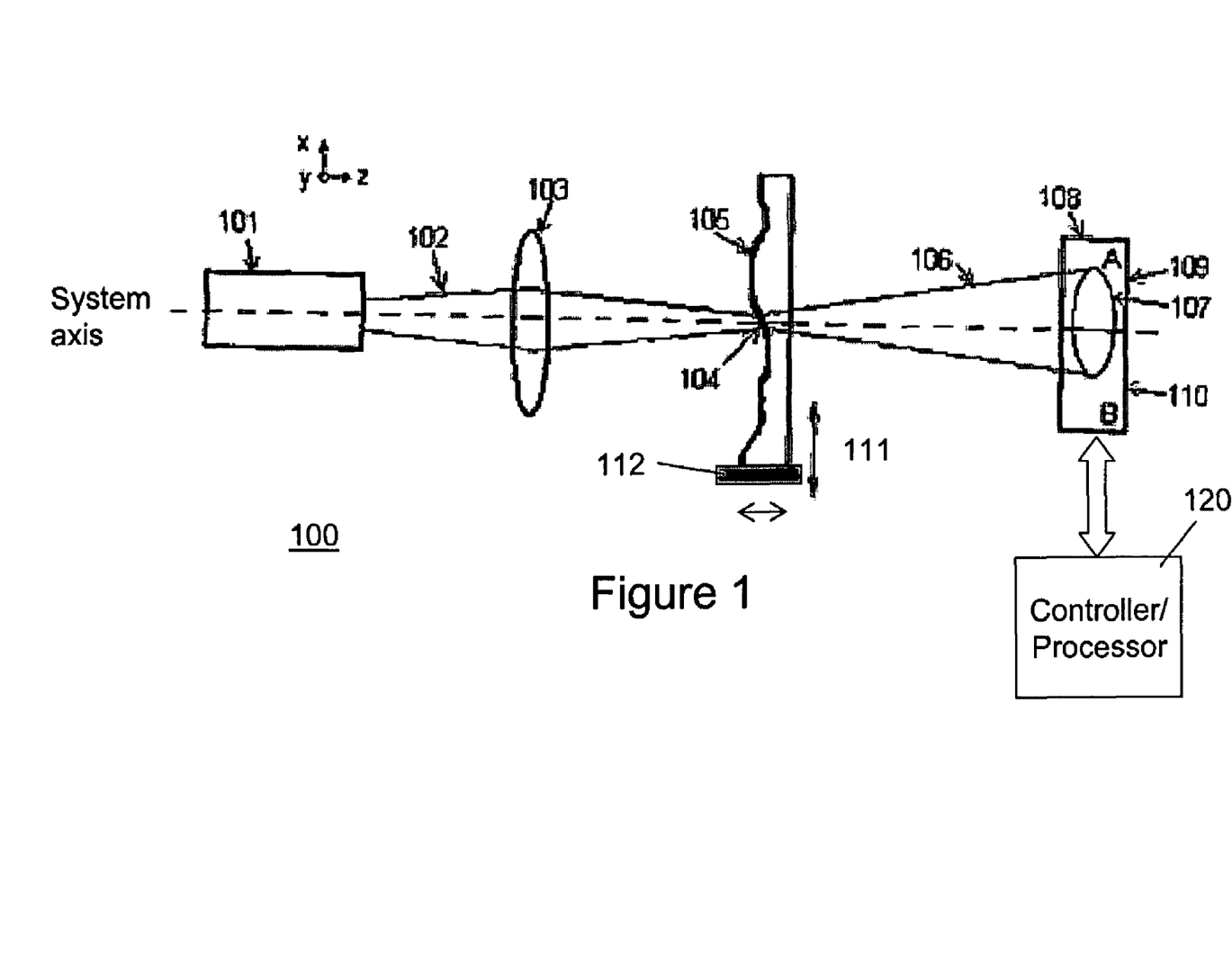
FIG. 1 illustrates an exemplary optical scanning system for measuring optical characteristics of a transmissive optical article.

FIG. 1 illustrates a two-dimensional schematic illustration of an exemplary optical inspection system 100. This particular example is configured in a transmission mode, e.g., where a probe beam 102 transmits through optical article 105 to sensor 108. In one example, illumination source 101 includes a coherent laser that produces probe beam 102. Probe beam 102 is focused by lens 103 to create focused spot 104 at a reference location on the expected position of the surface of (or within) optical article 105. In one example, lens 103 has a high numerical aperture, e.g., up to approximately 0.3 for an approximately 2 mm sample article. In other examples, a numerical aperture of approximately 0.6 may be used and may also include spherical aberration compensation. The spot 104 is focused to a reference plane located on or within optical article 105. For example, the reference plane may be located at or near a surface of article 105. In other examples, the reference plane may be located at various distances within the volume of article 105.

Article 105 may include a wide variety of optical articles including, but not limited to, an optical lens, prism, multilayer optical element (including reflective and transmissive portions), thin or volume hologram, biological specimen, optical storage device, holographic storage device, and the like. In the case of optical storage devices such as holographic storage devices, the exemplary methods and system may be used to inspect the optical quality of the article or be used in a manner to read data stored therein, for example, user data or servo tracks.

Surface and/or index variations of article 105 may cause diffraction or refraction of probe beam 102 such that emerging probe beam 106 is potentially deflected from its original beam path along the system axis. The deflection of the path of probe beam 106 relates, at least in part, to characteristic of optical article 105 such as surface variations and index variations. It should be noted that the term "diffraction" and "refraction" are used interchangeable herein to refer generally to the change in direction or redistribution of the propagation and intensity of electromagnetic radiation, e.g., light waves, that result form an object in the path of the light waves causing variations of one or more of amplitude, phase, or direction of the light waves. Optical articles, whether reflective or transmissive, may deflect probe beam 106 from its original beam path via diffraction and refraction alone or in combination.

The emerging probe beam 106 propagates to form spot 107 on the surface of sensor 108. Sensor 108 is centered with the path of original probe beam 102 such that an off center incident probe beam 106 and spot 107 on sensor 108 indicate a deflection of probe beam 106 from its original probe path. In this example, for the illustrated upward probe beam deviation, photodetector segment 109 will detect higher intensity than photodetector segment 110. Each segment 109 and 110 will generate a signal associated with the relative intensity of light received, which indicate to controller/processor 120 the deviation of the beam. The data from this portion of optical element is recorded and optical element 105 is repositioned to another point along scanning axis 111, where the process is repeated. It should be noted that probe beam 106 may form a non-uniform spot 107 on sensor 108; for example, the light may be scattered and distributed in various irregular patterns on sensor 108.

In one example, sensor 108 includes a segmented photodetector having two or more segmented sections, e.g., four sections. Each section of the segmented photodetector produces a signal associated with the intensity of light incident thereon allowing a determination of the angle of the probe beam 106 emerging from optical article 105. In one example, an On-Trak PSM2-4Q quadrant detector, manufactured and sold by On-Track Photonics, Inc., may be used. In another example, sensor 108 may include a position sensitive diode device, wherein the device outputs two signals which allow for the determination of positional information of the centroid of light energy incident thereon. In one example, an On-Trak PSM2-4 position sensitive diode, manufactured and sold by On-Trak Photonics, Inc., may be used. A first signal from a position sensitive diode device provides information regarding the position of a light intensity centroid along the x-axis of the sensor, and the second signal provides information regarding the position of a light intensity centroid along the y-axis of the sensor, where the centroid averages position weighted by intensity. Those of ordinary skill in the art will recognize that various other optical sensors not specifically mentioned may be used.

The exemplary optical system 100 may further include a stage 112 for supporting and translating optical article 105 during scanning processes. Stage 112 may translate article 105 in the x and y direction as indicated in FIG. 1. In other examples, the optical system including illumination source 101, lens 103, and sensor 108 may translate relative to article 105 during scanning processes. Alternatively or additionally, in one example, stage 112 may translate article 105 in the z direction, as indicated in FIG. 1, to vary the location of spot 104 within article 105. In other examples, illumination source 101 and/or lens 103 may be translated along the axis to vary the location of spot 104 along the z direction.

The exemplary optical system 100 further includes a controller/processor 120 in communication with system 100. Controller/processor 120 may include any suitable controller or microprocessor in communication with sensor 108, illumination source 101, repositioning mechanisms of stage 112, and the like. In other examples, separate controllers/processors may be contact with different portions of system 100, e.g., sensor 108 and stage 112. The exemplary inspection and scanning methods may be carried out by system 100 (including controller/processor 120) in one or more of firmware, software, and hardware.

Those of ordinary skill in the art will recognize that the exemplary systems illustrated and described may include various additional optical components such as lenses, prisms, apertures, filters, beam splitters, gratings, imaging or pick-up lenses, beam conditioning optics, and the like. For clarity, however, such additional features have been omitted from the description. Additionally, the exemplary scanning methods may be carried out by moving the article and/or the optical system relative to each other with any suitable mechanisms to scan various locations of the optical article. The relative motion may include relative motion in all dimensions (x, y, and z) to perform surface and volumetric scans.

Figure 2:
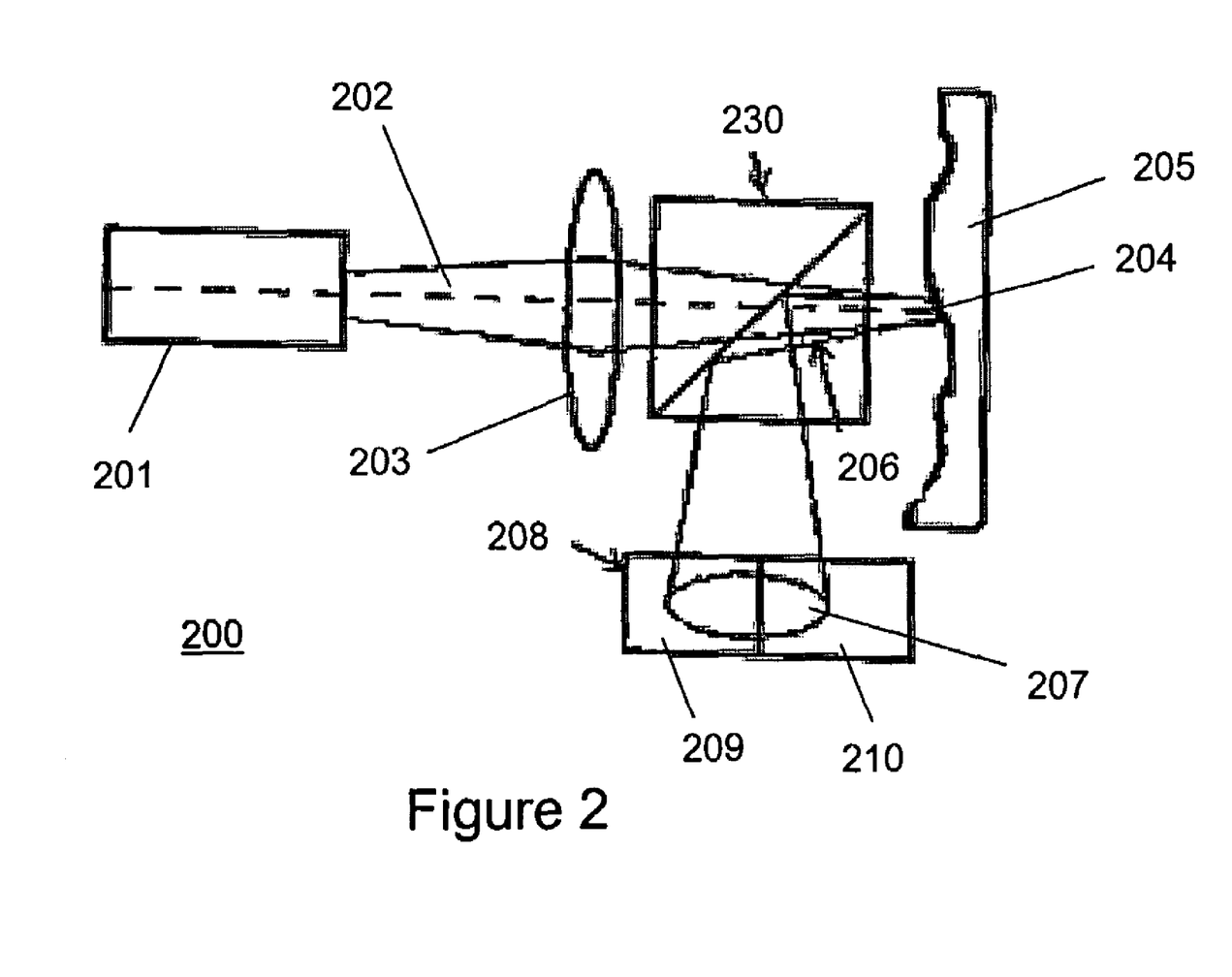
FIG. 2 illustrates an exemplary optical scanning system for measuring optical characteristics of a reflective optical article.

FIG. 2 illustrates another exemplary optical inspection system 200. This example is configured in a reflection mode, e.g., where the probe beam 206 is incident sensor 208 after reflecting from optical article 205. This configuration is similar to FIG. 1 described above, except that beam splitter 230 has been inserted into the path of probe beam 202 from illumination source 201 such that deflection of reflected beam 206 may be measured with sensor 208, e.g., a segmented photodetector, position sensitive diode device, or the like. Similarly, the probe beam 202 may be scanned in all dimensions to perform surface or volume scans of optical article 205. It should be noted that reflection of probe beam 202 may occur on a surface of optical article 205 as well is within the volume of optical article 205.

In another example, an optical inspection system may include both a reflection mode (illustrated in FIG. 1) and a transmission mode (illustrated in FIG. 2), and may be selectively or simultaneously implemented to inspect and scan an optical article. For varying materials, surface profiles, layers, and the like, it may be advantageous to measure light that is transmitted through and/or light that is reflected from portions of an optical article. Accordingly, a system may simultaneously detect deflection and intensity of a probe beam with a reflection and transmission configuration.

Figure 3:
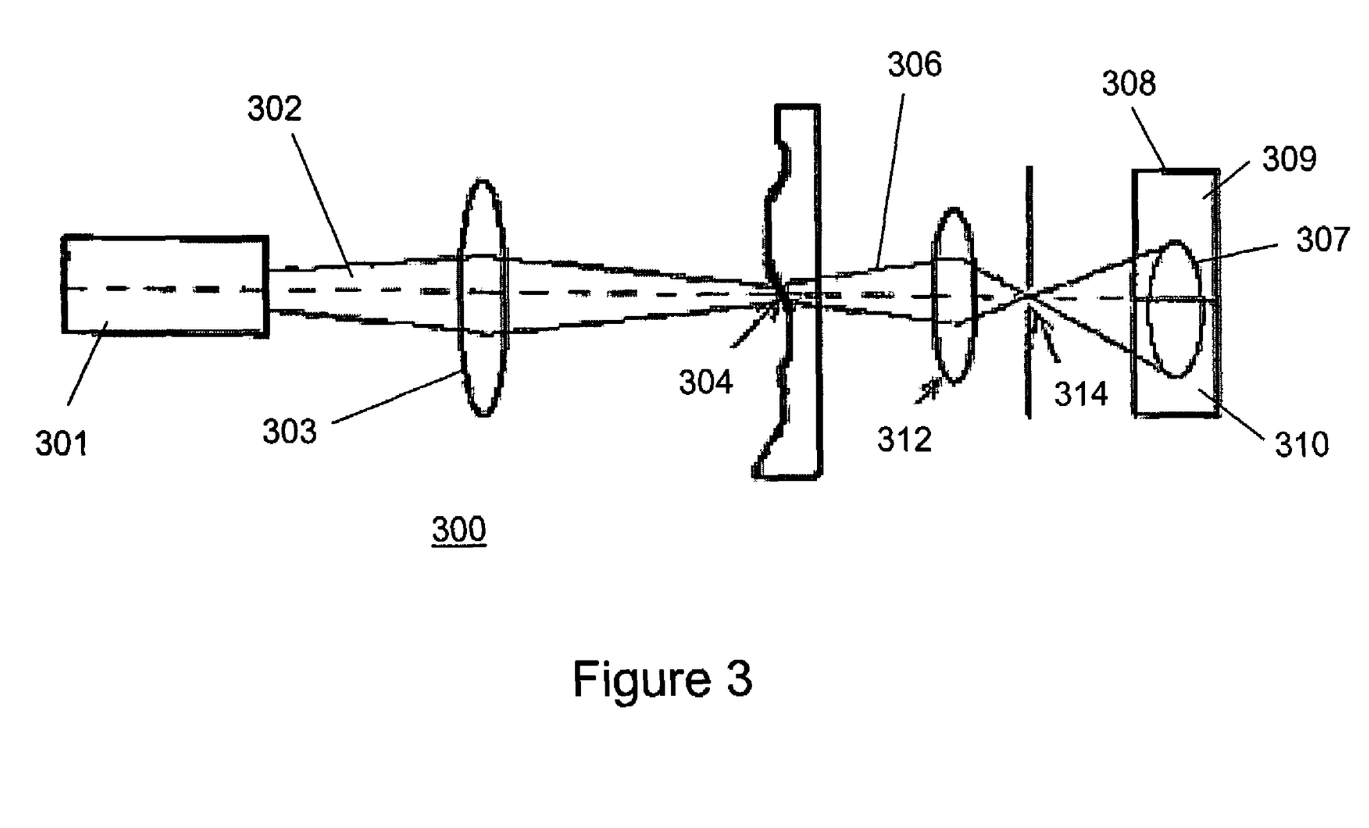
FIG. 3 illustrates an exemplary optical scanning system using confocal filtering techniques for measuring optical characteristics of an optical article.

In the exemplary optical inspection system illustrated in FIG. 1, the probe beam 102 may be deviated (e.g., diffracted, refracted, etc.) not only in the region of the focused spot 104, but also at the other surfaces and/or throughout the volume of optical article 105 under inspection. Deviations caused by other surfaces and/or index variations of the volume other than at focused spot 104 may create noise in the detected beam. FIG. 3 illustrates another exemplary optical inspection system 300 including a confocal lens or imaging system, which may advantageously filter the deflected beam and allow for separate measurement of specific depth planes (whether at a surface or within a volume of an optical article). The configuration of FIG. 3 operates in a manner similar to FIG. 1, except that confocal lens 312 is inserted into the exiting probe beam path 306. The confocal lens 312 is positioned such that an image of focused spot 304 is formed at pinhole 314 and directed to sensor 308. In this configuration, rays (or images) that are deviated at the reference plane of focused spot 304 will pass through pinhole 314. Rays deviated elsewhere in the volume will be blocked or filtered out from sensor 310 by the edges of pinhole 314, and hence will fail to affect the measurement of deflection.

The system of FIG. 3 is advantageously used to perform surface or volumetric scans of optical article 305 by optical article 305 relative to system 300 including probe beam 302, confocal lens 312, pinhole filter 314, and sensor 308. In addition to scanning the optical article for inspection purposes, exemplary scans described (whether in two or three dimensions) may be used to detect stored information. For example, a scan may be used to detect pits on or within an optical storage device or fringes within a holographic storage medium associated with stored information or data.

Figure 4:
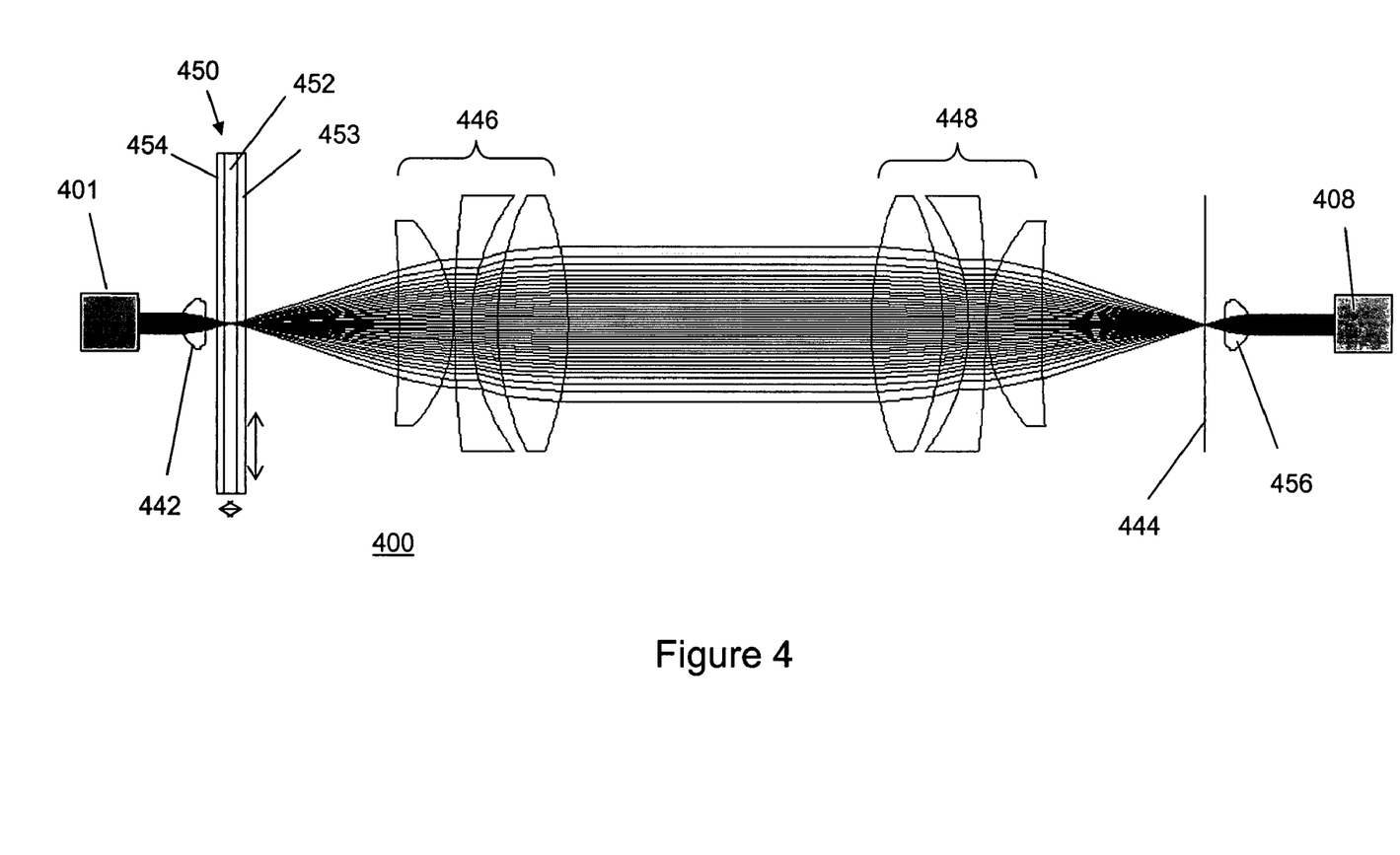
FIG. 4 illustrates an exemplary optical scanning system for measuring an optical characteristic of an optical article including a confocal imaging system.

FIG. 4 illustrates an exemplary volumetric scan system 400. Illumination source 401 produces light which is focused by an objective lens 442 to a reference location on or within optical article 450. Objective lens 442 may include an aspheric lens such as a Geltech Glass Aspheric Lens model no. 350340 or the like. Optical article 450 may include a multilayer device including outer layers 453 and 454 on opposing major surfaces of inner layer 452. In one example, the multilayer device includes a holographic storage device where inner layer 452 includes a suitable holographic storage medium and outer layers 453 and 454 include protective layers. In this example, the probe beam is focused to a reference plane and location at a portion of inner layer 452. Optical article 450 may be translated orthogonally with respect to the probe beam path as well as parallel to the probe beam path to provide a volumetric scan of optical article 450. Alternatively or additionally, one or more optical components of system 400 may be translated with respect to optical article 450 in all dimensions to provide a volumetric scan.

The emerging and potentially deflected probe beam is received and collimated by relay optics 446 and directed to relay optics 448. In this example, relay optics 446 and 448 may include OptoSigma triplet 027-0120 sold by OptoSigma Corp.; however, various other relay optic systems and lens sets may be employed. Relay optics 448 receive the collimated probe beam and focus the probe beam to pin-hole filter 444. Pin-hole filter 444 confocally filters out images other than the focused image at optical article 450. The emerging probe beam is received by optical element 456 and directed incident upon sensor 408, e.g., a position sensitive diode or the like. Optical element 456 may also include an objective aspheric lens such similar to objective lens 442. Sensor 408 may include any suitable device and communicate with a suitable analyzer or processor for receiving signals from sensor 408 as described previously. System 400 may scan article 450 in two or three dimensions and determine characteristics of optical article 450 such as index variations, surface features, and the like.

Figure 5:
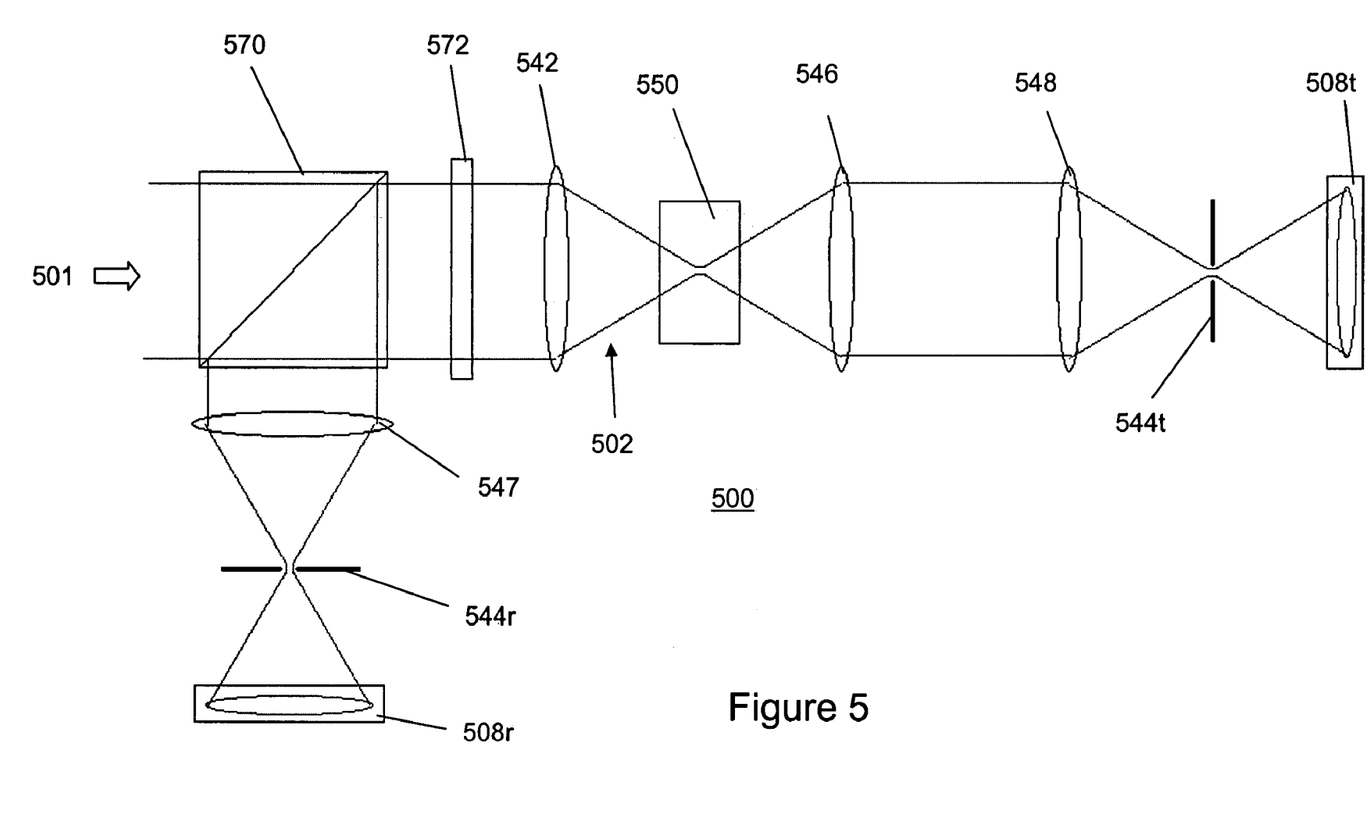
FIG. 5 illustrates an exemplary optical scanning system for measuring an optical characteristic of an optical article including a transmissive and reflective mode.

FIG. 5 illustrates an exemplary volumetric scan system 500 including a first sensor 508t for a transmission mode and a second sensor 508r for a reflection mode. Further, the transmission and reflection mode both include a confocal imaging system to perform, for example, volumetric scans of optical article 550. In operation, light 501 passes through beam splitter 570, quarter wave plate 572, and objective lens 542, which focuses probe beam 502 to a reference location within optical article 550. A portion of probe beam 502 may transmit through optical article 550 to the transmissive portion of system 500. Relay lenses 546 and 548, which may include a 4F configuration, relay and image the probe beam to a pinhole of filter 544t. Relay lenses 546 and 548 may include additional or fewer elements to direct an image through filter 544t in a confocal imaging system. The image emerging from filter 544t is detected by sensor 508a as described above.

Additionally, a portion of probe beam 502 may reflect from optical article 550. In this instance, the reflected probe beam is directed by objective lens 542 through quarter wave plate 572 and to beam splitter 570. Beam splitter 570 directs the reflected probe beam to a condenser lens that images the beam through pin-hole filter 544r (e.g., in a confocal imaging system) and to sensor 508r. Sensor 508r may be similar or different than sensor 508t.

The above exemplary systems are illustrative only; those of ordinary skill in the art will recognize that various modifications (including additions, subtractions, and substitutions of elements) not specifically mentioned are possible and contemplated. Modifications may be based on particular applications, optical articles, desired accuracy, size of the system, financial considerations, or the like.

Figure 6A:
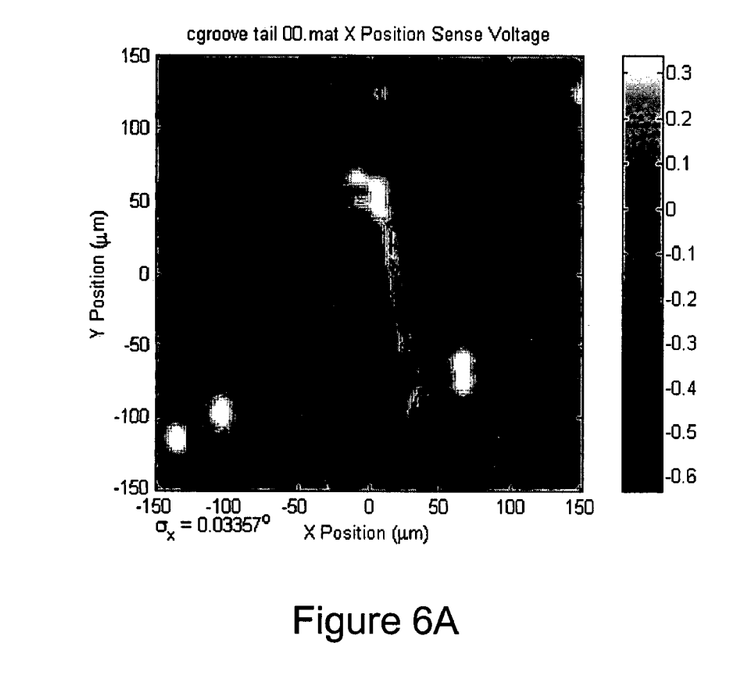
FIGS. 6A and 6B illustrate exemplary plots generated with data from a scanned optical article.
Figure 6B:
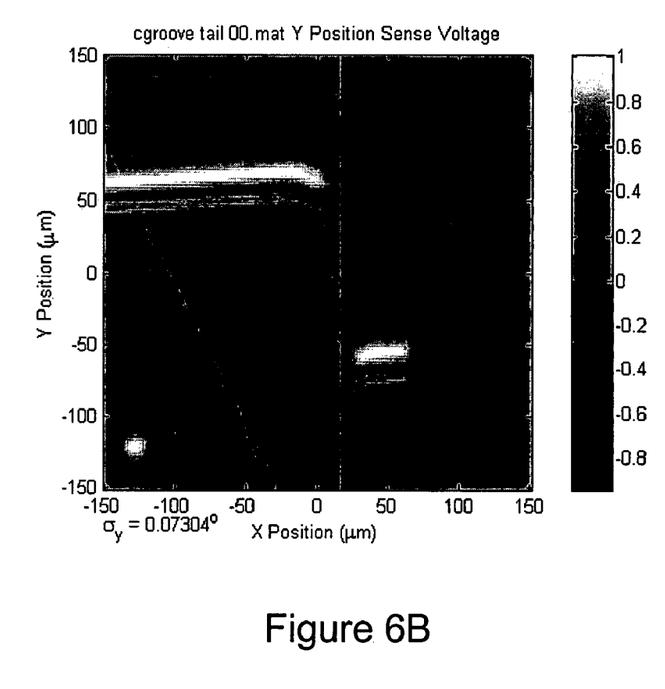

FIGS. 6A and 6B illustrate experimental data collected from an optical scanning system similar to FIG. 1. The light source included a DVD laser diode at 4 mW and 635 m. The optical article was translated by Newport MFN25PP translation stages sold by Newport Corporation. In this example, both transverse axes (x and y) were scanned, and a quadrant photodetector was used such that beam deflection could be measured along both the x and y axes. The optical article was a test sample; a flat plastic substrate etched with 270 nm deep groove features. The sample inspection points were taken at a 2 μm pitch in both the x and y scanning directions, and the focused spot was approximately 20 μm in diameter. FIG. 6A shows a false-color map of the beam deviation in the x-direction, while FIG. 6B shows the deviation in the y-direction (both shown in arbitrary units). FIGS. 6A and 6B clearly show the etched groove features, as well as scratches and other surface/index irregularities of the sample. The scanned deflection angles were plotted using Matlab software; of course, various other programs may be used to plot or analyze scanned data.

Figure 7A:
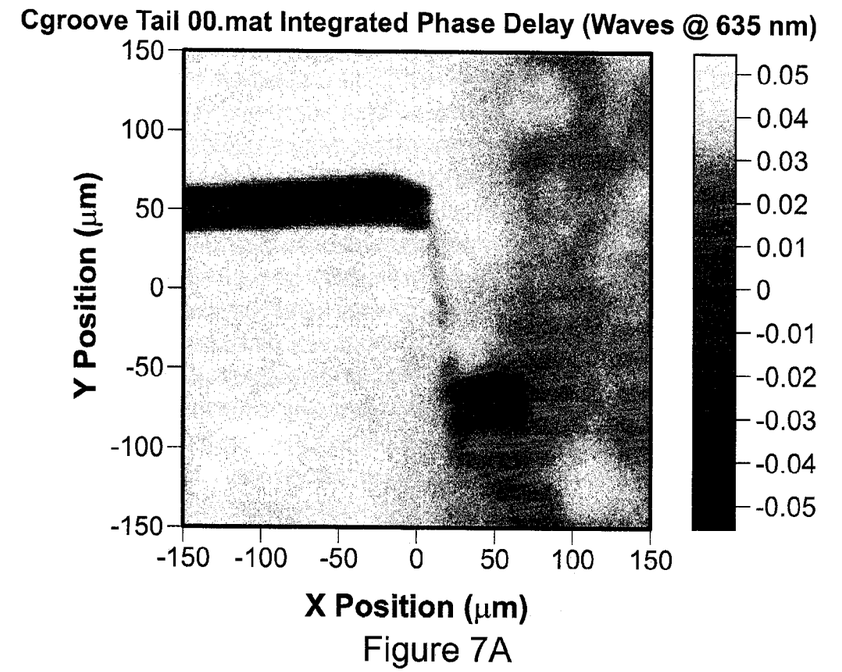
FIGS. 7A and 7B illustrate exemplary plots generated with data from a scanned optical article.
Figure 7B:
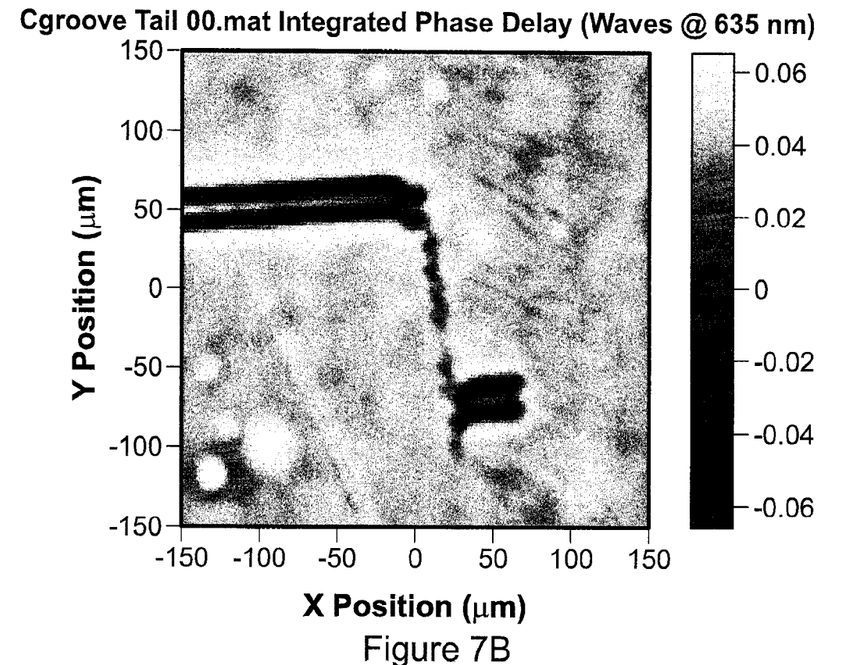

Additionally, FIGS. 7A and 7B illustrates exemplary plots from an optical scan (similar to FIGS. 6A and 6B) after exemplary numerical integration techniques. Each point or location in the probe beam focus during a scanning process is potentially deviated by the local index gradient (or surface angle). The deflection data is a convolution of the probe beam focus intensity profile, I(x,y) and the index gradient:

$$PSD_X(x, y) \propto I(x, y) * \frac{dn(x, y)}{dx}$$

$$PSD_Y(x, y) \propto I(x, y) * \frac{dn(x, y)}{dy}$$

where PSD refers to the raw data from the position sensor diode. The Fourier transform of the relationship provides:

$$PSD_X(\nu_x,\nu_y) \propto I(\nu_x,\nu_y) i \nu_x n(\nu_x,\nu_y)$$

$$PSD_Y(\nu_x,\nu_y) \propto I(\nu_x,\nu_y) i \nu_y n(\nu_x,\nu_y)$$

Solving for the index, n, results:

$$n(\nu_x, \nu_y) \propto \frac{PSD_X(\nu_x, \nu_y)}{i\nu_x I(\nu_x, \nu_y)}$$

$$n(\nu_x, \nu_y) \propto \frac{PSD_Y(\nu_x, \nu_y)}{i\nu_y I(\nu_x, \nu_y)}$$

The inverse Fourier transform is therefore:

$$n(x, y)_1 \propto \mathcal{F}^{-1}\left\{\frac{PSD_X(\nu_x, \nu_y)}{i\nu_x I(\nu_x, \nu_y)}\right\} \quad \text{Equation 1a}$$

-continued $$n(x, y)_1 \propto \mathfrak{J}^{-1}\left\{\frac{PSD_Y(v_x, v_y)}{iv_y I(v_x, v_y)}\right\}$$ Equation 1b The exemplary numerical integration provides two separate estimates of the index, where $n_1$ indicates the index features that change in the x direction, and $n_2$ indicates the index features that change in the y direction. In one example, the two estimates are averaged together to provide a potentially better estimate of the index value as follows:

$$\hat{n}(x, y) = \frac{(n(x, y)_1 + n(x, y)_2)}{2}$$

FIG. 7A illustrates a plot of an exemplary method for estimating the index values where $I(v_x,v_y)$ is set to 1 (i.e., $I(v_x,v_y)=1$) in equations 1a and 1b. This method is equivalent to assuming that the probe beam is a delta function, e.g., the method does not deconvolve the probe profile by boosting high frequencies and potentially increasing noise.

In another technique, of which FIG. 7B illustrates a plot, the values of $v_x$ and $v_y$ in the denominators of equations 1a and 1b are omitted. These terms generally increase low frequencies in accordance with the numerical integration, and may increase low frequency noise. Accordingly, omitting the terms may increase accuracy of the estimated index values.

Figure 8:
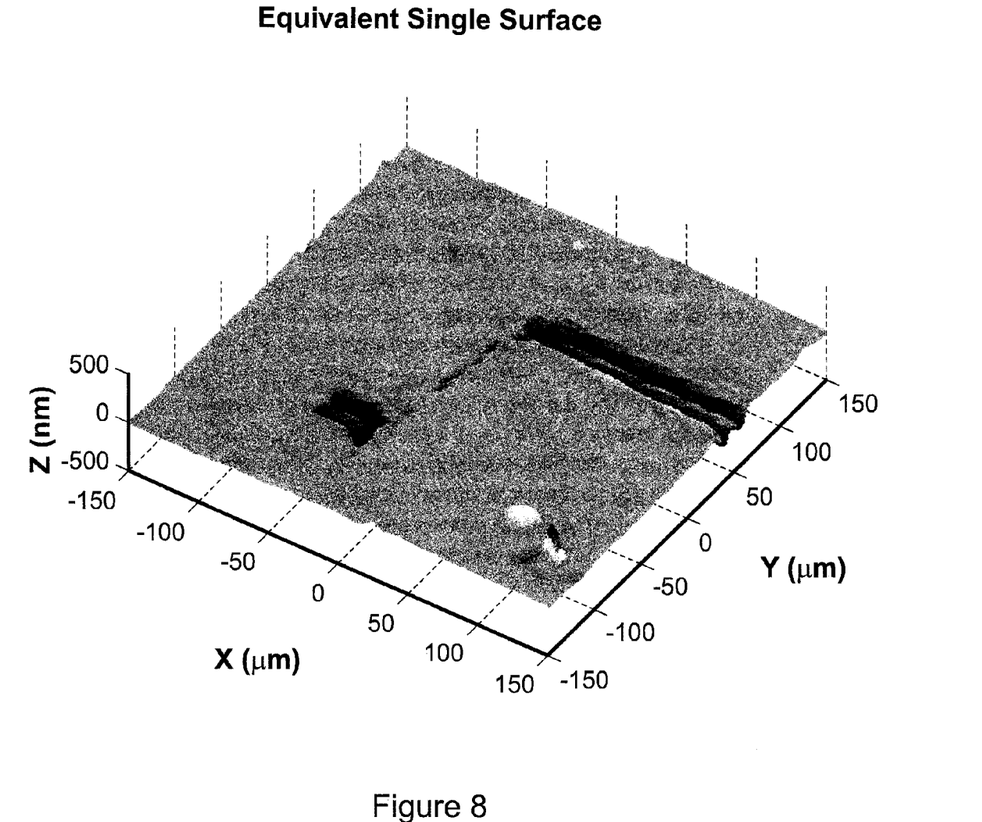
FIG. 8 illustrate an exemplary plot of an equivalent single surface with data from a scanned optical article.

FIG. 8 illustrates an exemplary equivalent single surface plot generated from optically scanned data. The data was collected from an optical scanning system similar to FIG. 1. An equivalent single surface plot may be created, in one example, by determining the phase scaling of integrated data by finding the effective surface angle from the raw $PSD_x$ and $PSD_y$ deflection angles based on the thin prism rule, for example:

$$\alpha_x = \frac{PSD_x}{(n_0 - 1)}$$

where $n_0$ is the (average) sample index, $\alpha$ is the effective surface angle, and $\alpha$ and PSDx are expressed in radians. The surface angle $\alpha$(=height per length) may be converted to height z during integration by scaling by the sample pitch, e.g., the separation scanned locations or data points in the x and y direction, and in this instance 2 µm. In another example, a known sample (e.g., a groove of calibrated depth) may be measured and the integrated data may be scaled accordingly.

It will be recognized by those of ordinary skill in the art that various other methods of using raw sensor data to create plots, analyze data, and the like, are possible. Additionally, methods for analyzing data may be carried out in one or more of firmware, software, and hardware.

The above detailed description is provided to illustrate exemplary embodiments and is not intended to be limiting. It will be apparent to those of ordinary skill in the art that numerous modification and variations within the scope of the present invention are possible. For example, various additional optical and mechanical elements may be included with the exemplary systems. Further, the apparatus and methods described herein should not be limited to any particular application, for example, the methods and systems are generally applicable for inspecting a wide range of optical devices and may also be applicable for a wide range of data retrieval methods and systems. Additionally, particular examples have been discussed and how these examples are thought to address certain disadvantages in related art. This discussion is not meant, however, to restrict the various examples to methods and/or systems that actually address or solve the disadvantages. Accordingly, the present invention is defined by the appended claims and should not be limited by the description herein.

The invention claimed is:

1. A system for measuring a characteristic of an optical article, comprising:
    a light source for producing light;
    an optical element for focusing the light along a probe path to converge at a reference location associated with an expected position of an optical article, wherein the reference location is moved during a scan to thereby focusing at least two different positions along an optical axis of the probe path;
    a sensor for detecting the light from the at least two different reference locations during the scan, wherein the sensor comprises a position sensitive diode device operable to generate two signals, a first signal associated with a location of an intensity centroid along one direction and a second signal associated with a location of an intensity centroid along a second direction, the second direction orthogonal to the first direction; and
    a processor, wherein the processor is configured to receive signals from the sensor associated with each spot of received light and determine a deflection angle and a direction of the deflection angle of the light from the probe path.

2. The system of claim 1, wherein the reference location is associated with an expected position of the surface of the optical article.

3. The system of claim 1, wherein the reference location is associated with an expected position within the optical article.

4. The system of claim 1, further including a stage for translating an optical article relative to the light source and the probe path in at least one dimension.

5. The system of claim 1, further including a stage for translating an optical article relative to the light source and the probe path in three dimensions.

6. The system of claim 1, wherein the processor is further configured to determine a characteristic of the optical article based on the deflection angle of the light at multiple locations of the optical article.

7. The system of claim 6, wherein the characteristic includes one or more of surface flatness, a divot feature, or a peak feature of the optical article.

8. The system of claim 6, wherein the characteristic includes an index of refraction value.

9. The system of claim 6, wherein the characteristic includes stored information.

10. The system of claim 1, wherein the position sensitive diode device generates two signals, a first signal associated with a location of an intensity centroid along one direction and a second signal associated with a location of an intensity centroid along a second direction, the second direction orthogonal to the first direction.

11. The system of claim 1, further including a second optical element positioned to focus the light beam from the reference location to a pinhole filter between the second optical element and the sensor.

12. The system of claim 11, wherein the second optical element and pinhole filter are disposed in a confocal imaging configuration.

13. The system of claim 1, where the sensor is positioned to detect light passing through the reference location.

14. The system of claim 1, where the sensor is positioned to detect light reflected from the reference location.

15. A method for measuring a characteristic of an optical article, comprising:
scanning an optical article with a focused beam of light;
detecting a deflection angle and a direction of the deflection angle of the focused beam of light from the optical article at multiple scan positions, wherein
the focused beam of light is focused during a scan to at least two different positions along an optical axis of the focused beam of light,
the deflection angle and a direction of the deflection angle for each of the multiple scan positions is determined from a single spot of light, and
for at least one of the multiple scan positions the focused beam converges within the optical article; and
determining a characteristic of the optical article based on the deflection angles at the multiple scan positions.

16. The method of claim 15, wherein the scan is performed along a first and second dimension, the first and second dimension orthogonal to the path of the focused beam of light.

17. The method of claim 15, wherein the focused beam of light from the optical article passes through a confocal imaging system.

18. The method of claim 15, further including producing a surface relief pattern from the multiple deflection angles.

19. The method of claim 15, further including producing an equivalent single surface plot from the multiple deflection angles.

20. The method of claim 15, further including producing a volumetric index map.

21. The method of claim 15, wherein the beam of light is detected with a position sensitive diode device.

22. The system of claim 21, wherein the position sensitive diode device is operable to generate two signals, a first signal associated with a location of an intensity centroid along one direction and a second signal associated with a location of an intensity centroid along a second direction, the second direction orthogonal to the first direction.

23. A system for measuring a characteristic of an optical article, comprising:
a light source for producing light;
an optical element for focusing the light along a probe path to converge at a reference location associated with an expected position of an optical article, the reference location within the optical article or on a surface thereof;
a sensor for detecting the light from the reference location, wherein the sensor comprises a position sensitive diode device operable to generate two signals, a first signal associated with a location of an intensity centroid along one direction and a second signal associated with a location of an intensity centroid along a second direction, the second direction orthogonal to the first direction;
a second optical element positioned to focus the light beam from the reference location to a pinhole filter between the second optical element and the sensor; and
a processor, wherein the processor is configured to receive signals from the sensor associated with a single spot of received light and determine a deflection angle and a direction of the deflection angle of the light from the probe path.

24. The system of claim 23, wherein the second optical element and pinhole filter are disposed in a confocal imaging configuration.

25. The system of claim 23, wherein the processor is further configured to determine a characteristic of the optical article based on the deflection angle of the light at multiple locations of the optical article.

26. The system of claim 23, wherein the characteristic includes one or more of surface flatness, a divot feature, or a peak feature of the optical article.

27. The system of claim 23, wherein the characteristic includes an index of refraction value.

28. The system of claim 23, wherein the characteristic includes stored information.

* * * * *